United States Patent
Forsythe et al.

(12)

(10) Patent No.: US 6,310,004 B1
(45) Date of Patent: Oct. 30, 2001

(54) SPROUT INHIBITOR METHOD

(76) Inventors: Darol Forsythe, 15401 Cartwright Rd., Boise, ID (US) 83703; John M. Forsythe, 4277 Balivi La., Nampa, ID (US) 83687

(*) Notice: Subject to any disclaimer, the term of this patent is extended or adjusted under 35 U.S.C. 154(b) by 0 days.

(21) Appl. No.: 09/416,231

(22) Filed: Oct. 12, 1999

Related U.S. Application Data

(63) Continuation of application No. 08/885,387, filed on Jun. 30, 1997, now Pat. No. 5,965,489.

(51) Int. Cl.$^7$ ............................ A01N 27/00; A01N 47/24
(52) U.S. Cl. ........................... 504/143; 504/304; 504/357
(58) Field of Search ................................... 504/143, 304, 504/357

(56) References Cited

U.S. PATENT DOCUMENTS

| | | | |
|---|---|---|---|
| 2,341,868 | 9/1944 | Hitchcock et al. | 47/58 |
| 3,128,170 | 4/1964 | Plant | 71/26 |
| 5,622,912 | 4/1997 | Riggle et al. | 504/143 |

FOREIGN PATENT DOCUMENTS

| | | |
|---|---|---|
| 1 203 394 | 4/1986 | (CA) . |

OTHER PUBLICATIONS

Shetty, Kiran K. et al., *Fine–Tuning Time for Inhibition*, Potato Grower of Idaho, Dec. 1993, pp. 14–15.

Dennis, Frank G., *Dormancy: Manifestations and Causes*, Chapter 20 in Handbook of Plant and Crop Physiology, Mohammad Pessarakli, ed. NY: Marcel Dekker, Inc., pp. 437–450. 1995.

*Primary Examiner*—S. Mark Clardy
(74) *Attorney, Agent, or Firm*—TraskBritt

(57) ABSTRACT

A method of treating potatoes sequentially with chemically-different sprout inhibitors is disclosed. Sprouting of stored potatoes may be eliminated or minimized by a treatment with CIPC followed sometime later by a treatment with a substituted naphthalene such as 1,4-DMN. Also, an initial treatment with 1,4-DMN soon after the potatoes are harvested may be advantageous in addition to the later treatments with CIPC and 1,4-DMN.

4 Claims, No Drawings

SPROUT INHIBITOR METHOD

CROSS REFERENCE TO RELATED APPLICATION

This application is a continuation of application Ser. No. 08/885,387, filed Jun. 30, 1997, now U.S. Pat. No. 5,965,489, issued Oct. 12, 1999.

BACKGROUND OF THE INVENTION

1. Field of the Invention

This invention relates to methods for treating tubers such as potatoes with sprout inhibitors to prevent sprouting during storage of said tubers.

2. State of the Art

It is well known in the art to treat tubers such as potatoes with various chemicals having sprout-inhibiting properties. CIPC (isopropyl-3-chlorophenyl-carbamate) has been conventionally used for this purpose for about 30 plus years. More recently, chemicals such as various isomers of dimethylnaphthalene and other substituted naphthalenes have exhibited for their sprout-inhibiting characteristics.

Considerable study and innovation have been directed towards inhibition of potato sprouting during storage in large storage facilities. U.S. Patents to Hitchcock et al., U.S. Pat. No. 2,341,868; Luck, U.S. Pat. No. 4,078,480; Vaughn, et al., U.S. Pat. No. 5,129,951; Morgan, U.S. Pat. No. 4,887,525; Plant, U.S. Pat. No. 3,128,170; and Riggle et al., U.S. Pat. No. 5,622,912 describe various treatments to prevent sprouting in storage facilities.

Potatoes when being dug are frequently bruised, cut and/or abraded. These injuries to the potatoes oftentimes cause spoilage during shipment, storage and the like. A process known as suberization occurs naturally which tends to heal many of these injuries. However, whenever potatoes are stored, which occurs with a particularly large portion of potatoes harvested in any given year, if healing occurs slowly, a significant loss of potatoes can occur through spoilage. Early treatment with certain sprout inhibitors, such as CIPC, may retard the suberization process, thus contributing to the loss of potatoes through spoilage.

For example, it is relatively common in the potato storage industry to treat potatoes with Chloroisopropyl-N-carbamate (CIPC) to prevent or retard development of sprouts in the potatoes. Even though untreated potatoes are stored at a cool temperature, for example, generally between about 40° and 45° F., sprouting does begin to occur after a month or more of storage. Storage of upwards of six to eight months is typical for a stored potato harvest. Thus, without treatment of a chemical such as CIPC, the stored potatoes become entangled in sprouts and the whole stored lot of potatoes may become economically useless. Although early treatment with CIPC could be advantageous for sprout inhibition purposes, application of CIPC is typically delayed until after suberization has occurred inasmuch as CIPC tends to retard suberization, resulting in accelerated rot and spoilage.

In potatoes, cell division and cell elongation of the tuber buds results in formation and emanation of sprouts from the tuber buds after the potato has entered a quiescent phase of dormancy that typically follows storage at or slightly above 45° F. Although tuber sprout formation can be suppressed by storage of the tubers at lower temperatures of from 38° to 39° F., the lower storage temperatures cause increased reducing sugar levels in the stored potatoes. Potatoes with increased levels of reducing sugars may turn brown when french fried, thereby producing an unacceptable food product.

To inhibit sprout formation in potatoes, synthetically derived sprout inhibitors, for example, tetrachloronitrobenzene, maleic hydrazide, and isopropyl-3-chlorophenylcarbamate (CIPC) also commonly referred to as chlorpropham, have been applied. CIPC is typically applied in one or two applications to the tubers to be stored using thermal fogging techniques. Conventional thermal fogging involving the application of CIPC into a stream of hot air or onto a hot surface of up to 1000° F., to produce a CIPC aerosol. The CIPC aerosol is circulated through potatoes piled in a potato storage building with the use of fans. Preferably the potatoes are firm rather than soft when treated with the CIPC aerosol, since a pile of softened potatoes may be substantially compressed thereby impeding distribution of the aerosol. CIPC residue levels, will, however, typically decrease over time due to biodegradation, venting and atmospheric loss. To extend he effective sprout inhibiting capability of CIPC, further applications may be needed.

However, it is becoming increasingly desirable worldwide to decrease the application of synthetically derived substances to fruits and vegetables during growth, storage and shipping. In particular, residue levels of CIPC are subject to regulation. So, while CIPC has been utilized to inhibit sprout formation in tubers for decades, its toxicology has been questioned and it is one of a number of synthetically derived substances whose residue levels are of concern to the U.S. Environmental Protection Agency.

In order to decrease use of synthetically derived substances such as CIPC, naturally occurring biological control mechanisms and substances are actively sought. Naturally occurring sprout inhibitors are known. For example, U.S. Pat. No. 5,436,226 for NATURAL SUPPRESSION OF SPROUTING IN STORED POTATOES USING JASMONATES claims a method of inhibiting sprouting of tubers by exposure to various forms of jasmonic acid, at some of which are naturally occurring compounds.

Also by way of example, Canadian Patent No. 1,203,394 teaches the use of dimethylnaphthalene (DMN) and diisopropylnaphthalene (DIPN) as potato sprout inhibitors. However, this patent teaches the need for application of DMN and DIPN with an inert carrier which implies the utility of DMN and DIPN alone as the active ingredient. However, long term effectivity of DMN and DIPN as tuber sprout inhibitors at lower residue levels under less than ideal circumstances has not been fully established.

Testing of isomers of dimethyl naphthalene (DMN) as a potential sprout inhibitor was conducted by placing alumina particles containing DMN in a box of potatoes stored at 10±0.5° C. in a ventilated cooler for a period of 12 weeks. The potatoes evidenced sprout inhibition in comparison with a control batch, i.e., in an untreated batch, and with a batch treated with Tecnazene, a commercial sprout inhibitor. Beveridge, et al., *The Assessment of Some Volatile Organic Compounds as Sprout Suppressants for Ware and Seed Potatoes, Potato Res.* 24 (1981) 61–76 and Beveridge, et al., *Dimethyl Naphthalene as a Sprout Suppressant for Ware and See Potatoes, Potato Res.,* 24 (1981) 77–88.

The use of DMN treatment in a large storage facility has also been proposed. In PCT application PCT/GB92/01482 (Int'l. Pub. No. WO 93102563) of Everett-Todd, a system for monitoring the vapor pressure of alkyl naphthalenes is disclosed wherein alkyl naphthalenes are added to the facility when the monitored vapor pressure of alkyl naphthalenes falls below a certain value, e.g., 5 mg of alkyl naphthalene per cubic meter of storage free space.

While considerable effort has been devoted to sprout prevention of potatoes stored in larger facilities, little or no effort has been devoted to prevention of sprouting of potatoes during shipment. Freshly-dug and stored potatoes are shipped to commercial markets, e.g., restaurants and the like, and to consumer markets, e.g., retail grocery stores, in refrigerated trailers and railroad cars. No other particular effort has been made to inhibit sprouting during the shipping and distribution process.

Riggle et al, supra., teach that simultaneous application of CIPC and DMN provides improved results over application of either sprout inhibitors separately.

Serial application of different sprout inhibitors have previously been conducted where the first sprout inhibitor, maleic hydrazide (MH 30) is applied to potato plants in the field well before the potatoes are harvested. Later, CIPC is applied via an aerosol to the harvested potatoes after they have been harvested and stored for a sufficient period that bruises and cuts have healed, i.e., suberization has occurred.

SUMMARY OF THE INVENTION

The instant invention relates to a method of inhibiting the sprouting of stored tubers, especially potatoes, by applying a first sprout inhibiting chemical to the stored potatoes and then applying a second sprout inhibiting chemical at a later time. The first chemical is preferably CIPC while the second chemical is preferably a substituted naphthalene and more preferably an isomer of DMN (dimethyl naphthalene), especially 1,4-DMN. The time elapsed between application of the first and second chemical applications may be from a few weeks to several months. The second chemical is generally applied at a time span when the efficacy of the sprout inhibiting characteristics of the first chemical is waning. Surprisingly, a very small addition of a second chemical, such as DMN when the first chemical is CIPC, is very effective in preventing sprouting for a long time after said second application.

One advantage of the invention is that CIPC residue in significant quantities has been considered very undesirable when potatoes, or other tubers, are eaten. The instant invention provides an effective anti-sprouting treatment protocol where very minimal amounts, i.e., safe residual amounts of CIPC are on the potatoes when consumed since the sprout inhibitor applied in the later stages of potato storage is not CIPC but a naturally occurring sprout inhibitor such as DMN, which may even be applied as the potatoes are being removed from storage, washed and packaged for shipment to stores.

Substituted naphthalenes useful in this invention include DIPN (Diisopropyl naphthalene), methyl naphthalene and isomers of dimethyl naphthalene, especially 1,4 DMN.

DETAILED DESCRIPTION OF THE INVENTION

The instant invention, in a preferred embodiment, comprises treating stored potatoes with an aerosol of CIPC to provide an effective residue upon the potatoes to prevent or inhibit sprouting for a period of at least several weeks to several months depending upon the conditions of storage. Potatoes are typically stored at temperatures less than about 50° F., with temperatures of about 42° to about 45° F. being preferable, under very humid conditions.

In a conventional storage situation at least a second application of CIPC is done before the potatoes are ultimately removed from storage. In the method of the instant invention, however, this second, and especially the last application of sprout inhibitor, if more than two applications are made, is done with a substituted naphthalene, especially DMN, so that minimal residues of CIPC exist when the potatoes are on a grocer's shelf.

In regard to the efficacy of DMN as a sprout inhibitor, reference is made herein to Reg. No. 67727 obtained by D-I-1-4 Inc. of Boise, Id. on Feb. 2, 1995 for aerosol grade sprout inhibitor containing 94.7% by weight 1,4-dimethylnaphthalene mix 5.3% inert ingredients. The recommended rate of application is one pound of active ingredient for 50,000 pounds of potatoes, which is a dosage of 20 ppm assuming all product.

According to the instant invention, a first application of CIPC is made at some time after the stored potatoes have completed their healing process and before sprouting has begun to occur, i.e., during the normal dormancy period of the potatoes at the particular conditions of storage. This first application of CIPC is typically done about three to six weeks after initial storage. The desired CIPC residue on the potatoes is from about four to about eight ppm, although higher and lower amounts are effective.

The CIPC may be introduced into a storage unit at a dosage rate of about 20 ppm, however, venting from the facility and other losses typically result in less than half the CIPC being deposited on stored potatoes.

A subsequent application of a substituted naphthalene, especially DMN, is done about four to ten weeks after the CIPC application with an elapsed time period between applications of about four to eight weeks being preferred depending upon the initial amount of CIPC residue on the potatoes. It has been discovered that the amount of DMN applied may be relatively small while still being effective. Residues of DMN in the range of 0.5 ppm to about 5 ppm are very effective. A very effective upper residue level for DMN has been found to be about 2 ppm.

In U.S. Pat. No. 5,622,912 to Riggle, it is taught that in the simultaneous application of both CIPC and DMN, i.e., from a composition containing both CIPC and DMN, the DMN concentration is preferably equal to or greater than the CIPC. Inventors have found, however, that in the serial or sequential application of CIPC first, later followed by DMN, the latter may be used in much smaller quantities than the CIPC. In fact, the outstanding sprout inhibition from such small quantities of DMN is a surprising feature of the instant invention.

In the serial or sequential application of first CIPC and then DMN, it is preferred that the DMN be made in smaller quantities than the CIPC although it is recognized that the use of DMN in larger quantities would also be effective and that smaller concentrations of CIPC may be initially applied followed by an earlier application, i.e. less elapsed time between applications, of DMN as the second sprout inhibitor.

While the inhibition of potato sprouting during storage is very desirable, that objective has been accomplished satisfactorily in the past by multiple treatments with CIPC. However, since the minimal presence of CIPC on potatoes at the time of consumption is greatly desired, sprouting is often a problem for potatoes during shipment to and storage by distributors, e.g. grocers and by consumers. This, to some extent, is as great a problem as sprouting during storage.

Surprisingly, DMN, even in small quantities, has proven effective in inhibiting sprouting of potatoes during the latter stages of storage and during shipment or storage by distributors and consumers when the potatoes had been earlier treated with CIPC. Storage by distributors is usually under adverse conditions of higher than desired temperatures and lower than desired humidities.

The initial treatment with CIPC may be conducted to deposit a residue of as high as 20 ppm if the treatment is 100% effective. However, because of a significant loss of CIPC in the aerosol process, the residue is typically less than about 10 ppm and may be much lower. Residues from 4 to 8 ppm are effective and common place. An initial CIPC residue of from as high as about 21 ppm to as low as about 2.5 ppm may be usefully applied. Residues as low as 2 ppm are effective for a short while under favorable storage conditions.

While the application of DMN is preferably low, e.g. about 0.5 ppm to about 2 ppm or less, e.g. 0.5 ppm, higher amounts may be used when storage conditions are unfavorable and the CIPC residue is very low.

Surprisingly, even when DMN is applied to potatoes having a residue of CIPC as low as about two ppm, treatment with a small amount of DMN, e.g. 0.5 ppm is very effective for an extended period of time, even when potatoes thereby treated are removed from controlled storage and subjected to high temperatures and low humidity conditions.

If three sprout inhibitor treatments are utilized, a first treatment with DMN at a level of about 0.5 to 2 ppm may be made even before the healing of cuts and bruises has occurred. A subsequent treatment may then be conducted with CIPC followed by a final treatment of DMN in the amounts and manner as described elsewhere herein.

The time period between treatments may vary from two or three weeks to one to two months depending upon the quantity of sprout inhibitor applied and the favorable conditions of storage.

EXAMPLE I

Test of Potatoes Treated with CIPC Initially and a Subsequent Treatment with DMN Potatoes stored in the fall at Winnemucca Farms, Nev., were treated once during controlled storage by thermal fogging of CIPC. The deposited residue was from about 5 ppm to 15 ppm depending on the location of the potatoes in the storage facility. In February of the following year potatoes were removed from storage, washed and placed in boxes. Such potatoes, even after washing, retained CIPC residue bonded to the skin, generally in an amount of about 2 ppm. No significant sprouting had occurred to the potatoes at the time they were removed from storage.

The potatoes, about 8 pounds per box, were then treated with 1,4-DMN by exposing the potatoes to vapors of such 1,4-DMN for a period of two weeks in an isolated environment, i.e. sealed conditions, however, the temperature experienced was room temperature-approximately 70° F. The method of application was by absorbing 1,4-DMN onto a paper blotter which was placed in each such box. The quantity of 1,4-DMN provided was sufficient to provide a residue of about 2 ppm.

This storage at room temperature simulated the conditions that stored potatoes experience when removed from storage and shipped to market. Even though the potatoes were experiencing stress due to the room temperature conditions, no significant sprouting occurred with such DMN treated potatoes containing CIPC residue in contrast to control samples which showed significant sprouting. The control potatoes had not been treated with DMN and contained only CIPC residue.

EXAMPLE II

Potatoes were treated in storage facilities by thermal fogging of CIPC to place a substantial residue of CIPC onto such potatoes, e.g. about four to eight ppm. A number of samples of these potatoes were removed about 30 days later, placed in boxes of approximately 40 pounds of potatoes per box. These boxes were treated with 1,4-DMN at a dosage rate of about 20 ppm, assuming 100% deposit, in the following manner:

Test A

Two boxes were exposed to DMN vapors for a period of 24 hours in a substantially sealed condition.

Test B

Two boxes were exposed to DMN vapors for a period of 48 hours in a substantially sealed condition.

Test C

Two boxes were exposed to DMN vapors for a period of five days in a substantially sealed condition.

The quantity of DMN provided was sufficient to give a residue of about two ppm if the DMN vapors were fully absorbed. Thus, the exposure for 24 hours would have resulted in less residue than the exposure for five days.

After treatment with DMN, the boxes were unsealed and exposed to ambient conditions, i.e. room temperature and humidity. Many of these potatoes, especially from Test C, exhibiting minimal sprouting even after seven months of exposure to non-controlled, ambient conditions. The results of this experiment were surprising in several aspects, namely:

1) That potatoes with only a minimal quantity of CIPC, e.g. 2 ppm or less, which if exposed to ambient (non-controlled) conditions for as little as a few weeks would exhibit substantial sprouting, could be treated with anything which could minimize or inhibit sprouting for such prolonged periods under ambient conditions.

2) That only a small amount of DMN, i.e. that sufficient to deposit residues of less than about 2 ppm would inhibit sprouting for prolonged periods at ambient conditions.

3) That treatment with CIPC, the most commonly used and most effective sprout inhibitor, even at much higher residues, e.g. 4 to 8 ppm or even much higher, would not have provided similar protection to such aged potatoes exposed for such an extended time period to ambient conditions.

Sprout inhibitors are generally effective for some period of time after application under controlled conditions of temperature and humidity. CIPC, for example, exhibits residues of 2 ppm and higher some several months after an effective initial application of residues as high as about 8 ppm. The CIPC is generally absorbed into the peel of the potato. The concentration of CIPC in the peel, at any given elapsed time after an application of CIPC, may be ten times the concentration determined as ppm based upon the whole weight of the potato. Thus, residues reported for a certain ppm value are indicative of the residue based upon the whole potato weight. Generally, it has been necessary when treating potatoes only with CIPC to do several treatments during a six to nine month storage period under controlled conditions to inhibit sprouting.

The residue of CIPC in a potato is determined by washing a whole potato to remove dirt, debris and the like. The whole potato is weighed and then quartered. The quarter portion is also weighed. The quarter portion is then pureed and the puree analyzed with a gas chromatograph to then determine the quantity of CIPC present. This quantity of CIPC is multiplied by a number determined by dividing the whole potato weight by its quarter portion weight (that quarter portion which was pureed). The total CIPC residue is then reported as parts per million (ppm) based upon the weight of the whole potato. This is the figure that is typically reported when identifying CIPC residue values.

The concentration of CIPC in a peel may be similarly determined by peeling a whole potato, weighing the peel and conducting the sample preparation and gas chromatograph analysis in a similar manner. The concentration of CIPC in the potato peel is typically many fold higher than the conventional residue value reported in literature based upon a whole potatoes weight.

Thus, CIPC may have a concentration in the peel of a potato from about 5 ppm to even about 20 ppm some three to six months after a single effective application of CIPC. An effective application is one which evenly distributes CIPC throughout a potato storage facility to an initial average residue level of about four to about eight ppm. (Some individual potatoes may, of course, have higher residue values while others may have smaller residue values.)

The USFDA has been concerned about the levels of CIPC in potatoes as they reach an individual consumer. This concern is heightened for potatoes which are baked because of the relatively higher concentration of CIPC in the potato peel in comparison to the body or pulp of the potato. This concentration of CIPC in the peel is unfortunate because many nutrients in potatoes tend to be concentrated in or adjacent to the peel.

The concentration of DMN residue present in a potato is determined by washing a whole potato, weighing the whole potato, quartering it and weighing the quarter. The quarter portion is pureed and then subjected to solvent extraction, e.g. by using hexane. The extract is then analyzed with a gas chromatograph. The quantity of DMN present is identified for the quarter portion. This value is multiplied by a figure determined by dividing the weight of the whole potato by the weight of the quarter portion. This value is reported as parts per million residue for the whole potato.

In U.S. Pat. No. 5,662,912 of Apr. 22, 1997 to Riggle et al. there are claims to a sequential treatment of potatoes with CIPC and then later with DMN. No support or teaching for such sequential treatment appears in the specification portion of the patent which teaches only the simultaneous application of CIPC and DMN at levels of 14 ppm and above (See Table II) for effectiveness. While it is indicated that CIPC levels may be as low as 2.5 ppm, it may also be inferred that a much higher residue of DMN would be applied in such a circumstance since the least level of CIPC shown in Table II is 14 ppm. Thus, the clear implication from Riggle's patent is that higher, e.g. four times as much DMN would be applied.

While the instant patent application has claims which overlap with Riggle, other claims are directed to a sequential treatment in which very minimal amounts of DMN may be utilized, amounts which are much less than 14 ppm and less than the CIPC residue. Nothing in Riggle teaches or suggests that a treatment with DMN of as little as 2 ppm or less would be effective for any purpose.

What is claimed is:

1. A method of inhibiting sprout formation in tubers during storage and post-storage comprising:

a) applying a first treatment of DMN to the potatoes; and b) applying a first treatment of CIPC to the potatoes at least about two weeks after said first DMN treatment.

2. The method of claim 1, wherein said first treatment with DMN provided a residue of about 0.5 to about 2 ppm of DMN.

3. The method claim 1, wherein a second treatment with DMN is made at least about two weeks after said CIPC treatment to provide a residue of at least about 0.5 DMN.

4. The method of claim 1, wherein said first treatment with CIPC provided a residue of about 4 to about 8 ppm of CIPC.

\* \* \* \* \*

UNITED STATES PATENT AND TRADEMARK OFFICE
CERTIFICATE OF CORRECTION

PATENT NO.    : 6,310,004 B1
DATED         : October 30, 2001
INVENTOR(S)   : Darol Forsythe and John M. Forsythe It is certified that error appears in the above-identified patent and that said Letters Patent is hereby corrected as shown below:

Column 2,
Line 17, change "he" to -- the --
Line 36, before "some" insert -- least --
Line 57, change "See" to -- Seed --

Column 6,
Line 16, change "scaled" to -- sealed --

Column 7,
Line 13, change "potatoes" to -- potato's --

Column 8,
Line 1, change "5,662,912" to -- 5,622,912 --

Signed and Sealed this

Seventh Day of October, 2003

JAMES E. ROGAN
*Director of the United States Patent and Trademark Office*